(12) United States Patent
Ichinohe et al.

(10) Patent No.: US 8,523,941 B2
(45) Date of Patent: Sep. 3, 2013

(54) INSTRUMENT FOR INSERTING INTRAOCULAR LENS

(75) Inventors: Takashi Ichinohe, Tokyo (JP); Kazunori Kudoh, Tokyo (JP)

(73) Assignee: Hoya Corporation, Tokyo (JP)

( * ) Notice: Subject to any disclaimer, the term of this patent is extended or adjusted under 35 U.S.C. 154(b) by 425 days.

(21) Appl. No.: 12/095,172

(22) PCT Filed: Dec. 1, 2006

(86) PCT No.: PCT/JP2006/324054
§ 371 (c)(1), (2), (4) Date: May 28, 2008

(87) PCT Pub. No.: WO2007/066586
PCT Pub. Date: Jun. 14, 2007

(65) Prior Publication Data
US 2009/0248031 A1 Oct. 1, 2009

(30) Foreign Application Priority Data
Dec. 8, 2005 (JP) .................. 2005-354968

(51) Int. Cl.
*A61F 2/16* (2006.01)
*A61F 9/00* (2006.01)

(52) U.S. Cl.
USPC ..................... 623/6.12; 606/107

(58) Field of Classification Search
USPC ........... 606/4, 166, 107, 108, 116; 623/6.12, 623/6.11; 604/59–64, 15–18; 221/198, 232, 221/279, 272
See application file for complete search history.

(56) References Cited

U.S. PATENT DOCUMENTS

| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |

(Continued)

FOREIGN PATENT DOCUMENTS

| DE | 3610925 | 10/1987 |
| DE | 4110278 | 10/1992 |

(Continued)

OTHER PUBLICATIONS

U.S. Appl. No. 13/757,790, filed Feb. 2, 2012.
U.S. Appl. No. 13/699,708, filed Jun. 8, 2011.

*Primary Examiner* — Kathleen Holwerda
*Assistant Examiner* — Jocelin Tanner
(74) *Attorney, Agent, or Firm* — Henricks, Slavin & Holmes LLP (57) ABSTRACT

An intraocular lens insertion instrument capable of smoothly pushing out a preset lens is provided. An intraocular lens insertion instrument comprises: a main body including a lens setting section on which a lens is set, a transition section that deforms the lens, and a nozzle piece that releases the lens; and a lens push-out mechanism that pushes out the lens set on the lens setting section. The instrument further includes a releasing means for releasing the lens pushed by the lens push-out mechanism from the lens setting section. The releasing means has a posture holding mount that holds the lens with a forward tilt relative to an axial line of lens movement. The posture holding mount has a passage through which the lens push-out mechanism passes.

17 Claims, 5 Drawing Sheets

(56) References Cited

U.S. PATENT DOCUMENTS

| | | |
|---|---|---|
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A * | 9/1998 | Chambers et al. ............ 606/107 |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A * | 2/1999 | Figueroa et al. ............ 606/107 |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |

| | | |
|---|---|---|
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 * | 12/2008 | Peterson et al. ............ 606/107 |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 2001/0007942 A1 | 7/2001 | Kikuchi et al. |
| 2002/0103490 A1 * | 8/2002 | Brady ..................... 606/107 |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 * | 6/2004 | Vincent ................ 623/6.12 |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0125000 A1 * | 6/2005 | Tourrette et al. .......... 606/107 |
| 2005/0182419 A1 | 8/2005 | Tsai |
| 2005/0222578 A1 * | 10/2005 | Vaquero ................ 606/107 |
| 2005/0261703 A1 | 11/2005 | Feingold et al. |
| 2006/0085013 A1 | 4/2006 | Dusek |
| 2006/0167466 A1 | 7/2006 | Dusek |
| 2006/0293694 A1 | 12/2006 | Futamura |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe et al. |
| 2009/0043313 A1 | 2/2009 | Ichinohe et al. |
| 2009/0112223 A1 | 4/2009 | Downer et al. |
| 2009/0204122 A1 | 8/2009 | Ichinohe et al. |
| 2009/0216244 A1 | 8/2009 | Pynson |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 08-024282 | 1/1996 |
| JP | 8-505540 | 6/1996 |
| JP | 09-506285 | 6/1997 |
| JP | 11-113939 | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | 2005/023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

* cited by examiner

INSTRUMENT FOR INSERTING INTRAOCULAR LENS

CROSS-REFERENCE TO PRIOR APPLICATIONS

This is a U.S. national phase application under 35 U.S.C. §371 of International Patent Application No. PCT/JP2006/324054, filed Dec. 1, 2006, and claims the benefit of Japanese Application No. 2005-354968, filed Dec. 8, 2005, both of which are incorporated by reference herein. The International Application was published in Japanese on Jun. 14, 2007 as International Publication No. WO 2007/066586 A1 under PCT Article 21(2).

TECHNICAL FIELD

The present invention relates to an intraocular lens insertion instrument used to insert an intraocular lens into an aphakic eye after cataract surgery or to an intraocular lens insertion instrument used to insert an intraocular lens to a phakic eye during refractive surgery. More specifically, the present invention relates to a preset intraocular lens insertion instrument wherein a lens has been preset in an injector.

BACKGROUND ART

In cataract surgery, there has been widely performed removal of opacified lenses by phacoemulsification (PEA) followed by implantation of intraocular lenses into aphakic eyes. Intraocular lenses are classified into hard intraocular lenses whose optics are made of a hard material such as PMMA and soft intraocular lenses whose optics are made of a flexible material such as silicone elastomer or soft acrylic. Upon use of a hard intraocular lens, the lens needs to be inserted through an incision having been cut in a cornea or sclera in a width approximately the same as the diameter of the optic of the lens. On the other hand, by folding the optic of a soft intraocular lens, the lens can be inserted through an incision smaller than the diameter of the optic. In order to reduce the risk of post-surgery corneal astigmatism or infection, insertion of a lens through a small incision is preferable. Consequently, soft intraocular lenses tend to be preferred. In addition, dedicated injectors having a mechanism to lead a lens to an eye through a slender tube are used in some cases in order to insert lenses into eyes. By using such injectors dedicated to intraocular lens insertion, a lens can be inserted through an incision smaller than 3 mm.

Recently, in order to eliminate the possibility of microbial contamination and operational mishandling at the time of dealing with lenses, preset injectors having lenses preset therein have been available on the market. Some of such preset injectors have a lens holding mechanism and a lens moving mechanism. The lens holding mechanism holds a lens inside of an injector in a state of non-stress on the optic of the lens so that the lens can be changed from a stationary state at the time of shipment to an operable state upon use. The lens moving mechanism moves the lens to a position where the lens can be moved by a push-out mechanism (see Patent Documents 1 and 2, for example).
Patent Document 1: Japanese Patent Application Laid-Open (JP-A) Publication No. 2003-325570
Patent Document 2: JP-A No. 2003-325572

DISCLOSURE OF INVENTION

Problems to be Solved by the Invention

Nonetheless, the moving mechanism to move the lens from the preset position to the releasable position is complex in the preset injectors described in the above-mentioned Patent Documents 1 and 2, which increases the production cost thereof. Moreover, the possibility of malfunctioning is not eliminated. In order to solve these problems, the inventors of the invention have invented a mechanism whereby a lens can be pushed out as it is at a preset position.

However, even in this mechanism, the lens may stick to the setting section in the case where an intraocular lens has been stored in close contact with a lens setting section of an injector. In this case, the lens is stressed excessively if the lens is pushed out parallel to a surface thereof, and may be damaged or become behaviorally unstable. Specifically, in the case where the lens is made of a soft acrylic material or a silicone material, the lens tends to stick more to the lens setting section. Furthermore, in a combination of the lens made of such a material and polypropylene or polyethylene generally used as a material of disposable injectors, the lens tends to stick even more to the lens setting section.

The present invention has been conceived in view of the above-mentioned problems, and an object of the present invention is therefore to provide an intraocular lens insertion instrument that enables smooth push-out operation of a preset lens.

Means for Solving the Problems

In order to achieve the object described above, the invention according to a first aspect thereof is an intraocular lens insertion instrument having: a main body comprising a lens setting section for setting an intraocular lens thereon, a transition section for deforming the intraocular lens, and a nozzle piece for discharging the intraocular lens; and a lens push-out mechanism for pushing out the intraocular lens set on the lens setting section, characterized in that the instrument further comprises a releasing means for releasing the intraocular lens pushed by the lens push-out mechanism from the lens setting section.

The invention according to a second aspect thereof is characterized in that the releasing means has a posture holding mount for holding the lens with a forward tilt relative to an axial line of lens movement.

The invention according to a third aspect thereof is characterized in that the posture holding mount has a passage through which the lens push-out mechanism passes.

The invention according to a fourth aspect thereof is characterized in that the lens push-out mechanism has a scooping surface for scooping the lens.

Effects of the Invention

According to the intraocular lens insertion instrument as the first aspect of the invention, the presence of the releasing means enables the lens in close contact with the lens setting section to be released from the lens setting section when the lens push-out mechanism pushes the lens. Therefore, the lens can be pushed out smoothly, and damage to the lens and unstable behavior of the lens can be prevented.

According to the intraocular lens insertion instrument as the second aspect of the present invention, the presence of the posture holding mount enables the lens to be held with the forward tilt relative to the axial line of lens movement. Therefore, when the lens push-out mechanism pushes the lens, the rear end of the lens is lifted, enabling air to move in between the lens and the lens setting section. In this manner, the lens can be released from the lens setting section and pushed out smoothly.

According to the intraocular lens insertion instrument as the third aspect of the present invention, the presence of the passage prevents the posture holding mount from hindering movement of the lens push-out mechanism at the time the lens push-out mechanism pushes the lens out. Therefore, the lens can be pushed out more smoothly.

According to the intraocular lens insertion instrument as the fourth aspect of the present invention, scooping the rear end of the lens by the scooping surface at the time of lens push-out enables air to move in between the lens and the lens setting section. Consequently, the lens is released from the lens setting section and can be pushed out more smoothly.

BRIEF DESCRIPTION OF THE DRAWINGS

FIG. 1 shows the overall structure of an intraocular lens insertion instrument of the present invention, in which (A) is a front view thereof and (B) is a plan view thereof.

FIG. 3 shows the structure of the lens setting section, in which (A) is a longitudinal cross-sectional view thereof while (B) is a transverse cross-sectional view thereof.

FIG. 4 shows modifications to a lens contact area, in which (A) is a longitudinal cross-sectional view thereof with a protruding lower end while (B) is a longitudinal cross-sectional view thereof with a diagonally cut lower end.

BEST MODE FOR CARRYING OUT THE INVENTION

Hereinafter, a preferred embodiment of the present invention will be described with reference to the accompanying drawings.

Figure 1A:
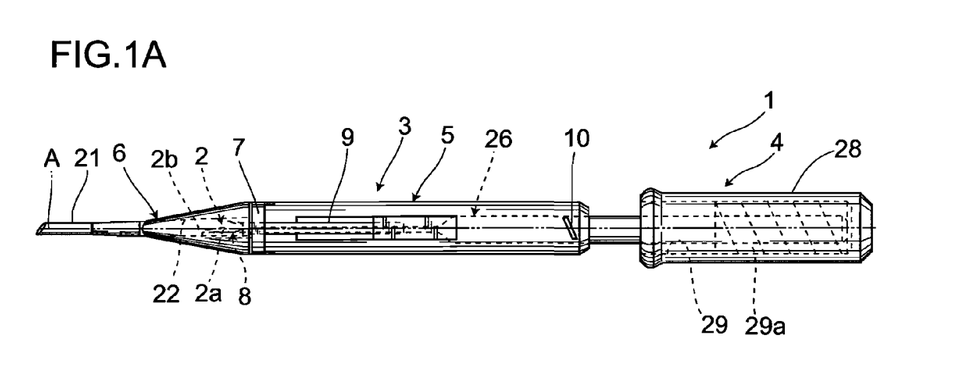
Figure 1B:
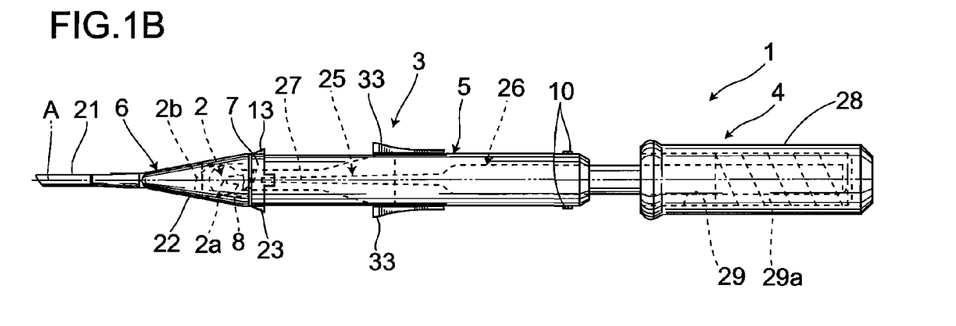

An intraocular lens insertion instrument 1 shown in FIG. 1 is used to discharge a deformable intraocular lens 2 (hereinafter simply referred to as the lens 2) safely and swiftly into an eye. The intraocular lens insertion instrument 1 is specifically a preset intraocular lens insertion instrument in which the lens 2 has been preset inside the instrument 1. More specifically, the intraocular lens insertion instrument 1 comprises a main body 3 that houses the lens 2 and inserts the lens 2 into an eye, and a lens push-out mechanism 4 that pushes out the lens 2. In this embodiment, a lens having an optic 2a and looped haptic elements 2b is used as the lens 2.

The main body 3 comprises a tubular proximal member 5 and a distal member 6 whose tapered end is relatively narrower than the proximal member 5. The proximal member 5 and the distal member 6 are united with each other in a detachable manner in an engagement section 7. Various materials can be used for the main body 3. For example, not only a metal such as stainless steel or titanium but also a synthetic resin or the like can be used for the main body 3.

The proximal member 5 has a lens setting section 8 at one end thereof and a slit 9 formed in a tubular sidewall thereof along a longitudinal direction thereof. Engagement projections 10 to engage with a grip unit that will be described later are formed on an outer periphery surface of the proximal member 5. The slit 9 is formed between an edge of the one end and a substantial center of the proximal member 5.

Figure 2:
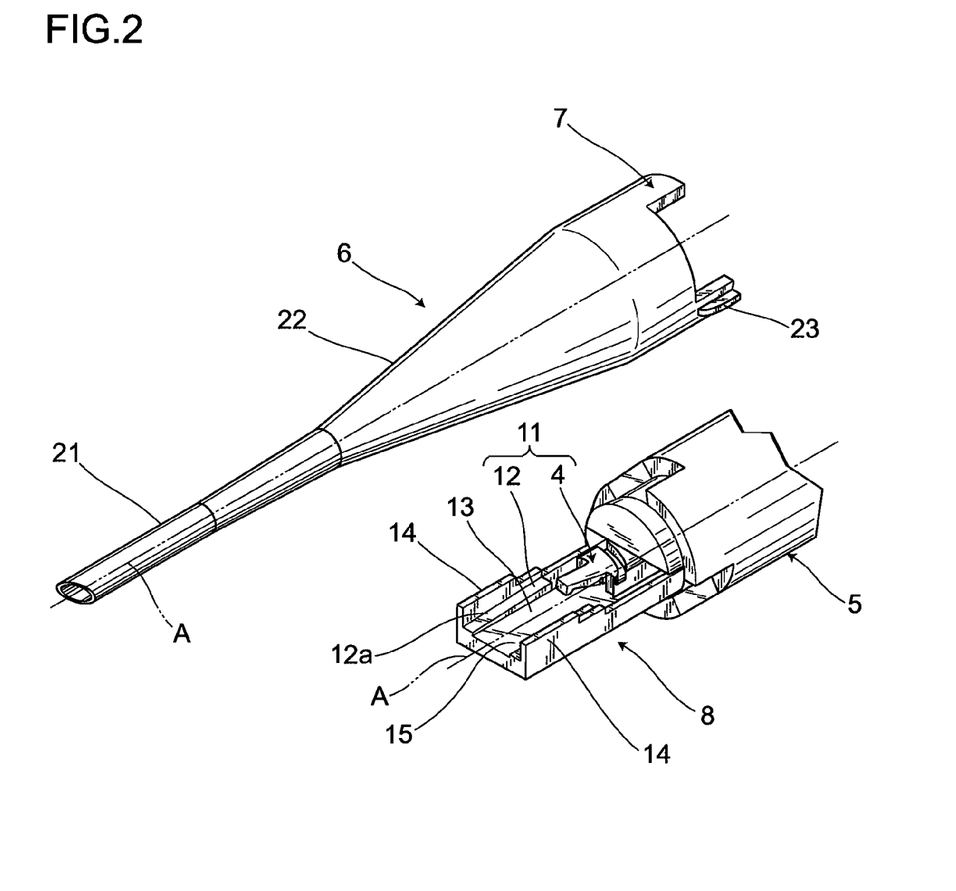
FIG. 2 is a perspective view showing the structure around a lens setting section.

The intraocular lens insertion instrument 1 has a releasing means 11 as shown in FIG. 2, whereby the lens 2 in close contact with the lens setting section 8 can be released and moved smoothly at the time the lens push-out mechanism 4 pushes the lens 2 having been set on the lens setting section 8.

The releasing means 11 releases the lens 2 from the lens setting section 8 by pushing forward the lens 2 stored on the lens setting section 8 with a forward tilt. The releasing means 11 comprises the lens push-out mechanism 4 and a posture holding mount 12 for holding the lens 2 on the lens setting section 8 with the forward tilt.

The lens setting section 8 comprises a setting section body 13 protruding from the one end of the proximal member 5, the posture holding mount 12 formed on an upper surface of the section body 13, and sidewalls 14 formed outside the posture holding mount 12. The setting section body 13 is made of a plate member whose surface is smooth and parallel to an axial line A of lens movement so that the lens 2 set thereon can be held stably.

The posture holding mount 12 is configured so as to hold the lens 2 with the forward tilt. On an upper surface of the posture holding mount 12, the mount 12 has slopes 12a inclined downward toward the distal end of the lens setting section 8. A passage 15 through which the lens push-out mechanism 4 passes is also provided in the center of the posture holding mount 12. The passage 15 comprises an elongated groove that is parallel to the axial line A of lens movement.

The sidewalls 14 are formed so that the center of the lens 2 can align with the axial line A of lens movement. The sidewalls 14 can also prevent the lens 2 from falling sideways when the lens 2 is placed on the lens setting section 8. Therefore, assembling the instrument becomes easy. The sidewalls 14 are made of plate members that protrude from both sides of the setting section body 13 and are elongated along a longitudinal direction of the body 13.

The distal member 6 comprises a nozzle piece 21 for inserting the lens 2 set on the lens setting section 8 into an eye, and a transition section 22 that connects the nozzle piece 21 with the proximal member 5. The transition section 22 is substantially funnel-shaped, tapering toward the distal end thereof, and connects the nozzle piece 21 at the distal end. The nozzle piece 21 is formed in such a size that an outside diameter thereof enables insertion thereof into an incision. The lens 2 is folded while passing through the transition section 22 by being pushed by the lens push-out mechanism 4. The distal member 6 also has a stopper 23 for stopping a hereinafter-described slider, at a predetermined position. The stopper 23 comprises projections that lock a hereinafter-described handling element of the slider.

As shown in FIG. 1, the lens push-out mechanism 4 comprises the slider 25 used for an initial operation to insert the lens 2, and a plunger 26 for inserting the lens 2 into an eye.

The plunger 26 is to insert the lens 2 folded by the slider 25 into an eye, and comprises a push rod 27 for pushing out the lens 2 and the grip unit 28 located at the proximal end of the push rod 27. The push rod 27 is loosely fitted into a hole 29 formed in the grip unit 28, and pivotally supported by the grip unit 28 at the bottom of the hole 29. A female screw 29a is formed in the hole 29. The female screw 29a formed in the grip unit 28 is to be screwed together with the engagement projections 10. The engagement projections 10 are made up of portions of a male screw that is to be screwed into the female screw 29a. Forming the engagement projections 10 as the male screw portions enables not only preventing of the engagement projections 10 from interfering with the slit 9 or the like but also secure screwing into the female screw 29a for pushing in the grip unit. The grip unit 28 thus pushes the push rod 27 along the axial line A of lens movement. The grip unit 28 is formed into a shape that enables easy push of the plunger 26.

Figure 3A:
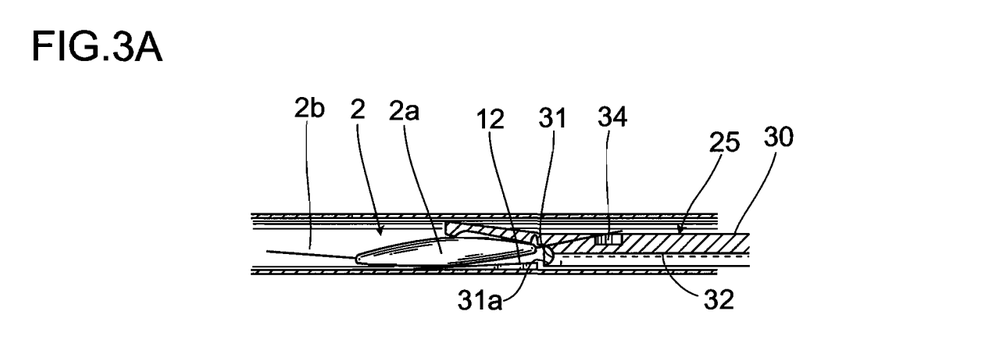
Figure 3B:
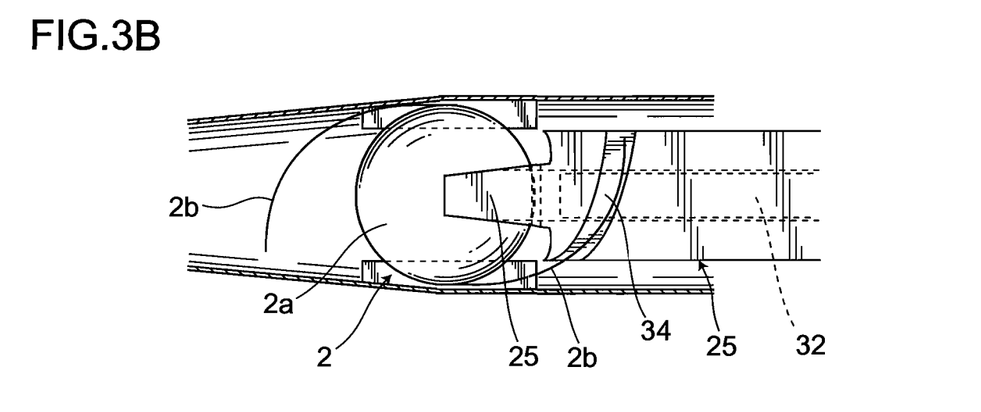

As shown in FIG. 3, the slider 25 is formed so as to enable the lens 2 set on the lens setting section 8 to be pushed out toward the distal end of the main body 3 without local stress on the lens 2 and to be folded in a predetermined direction. The slider 25 engages with the slit 9 in the main body 3. The slider 25 comprises a slider body 30 that supports the slider 25 along the axial line A of lens movement, a lens contact area 31 in contact with the lens 2 in an area larger than the plunger 26, a guide groove 32 that supports the plunger 26 along the axial line A of lens movement and functions as an insertion passage, and a looped-element guide 34 that catches one of the looped haptic elements 2b of the lens 2.

The lens contact area 31 is formed by an arc whose curvature radius is substantially the same as that of the outside diameter of the lens 2. The form of the lens contact area 31 enables smooth execution of the initial operation without locally stressing the lens 2, by contacting the lens 2 in a larger area.

The lens contact area 31 also has a scooping surface 31a. The scooping surface 31a enables scooping of the rear end of the lens 2 set on the lens setting section 8. The scooping surface 31a is shaped into a downward slope toward the distal end thereof. By having the sloped shape, the scooping surface 31a can gradually scoop up the lens 2, which enables more secure release of the lens 2.

Figure 4A:
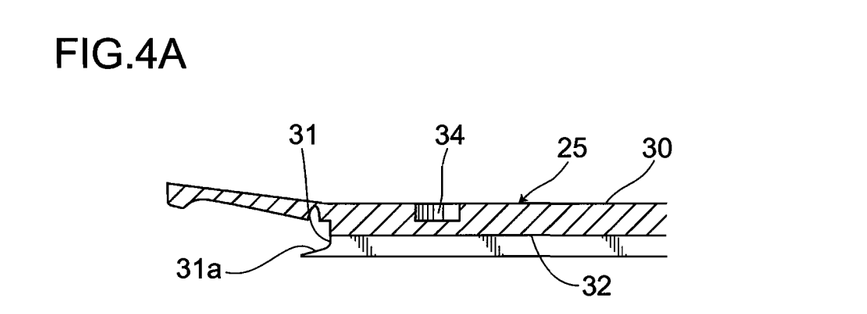

As shown in FIG. 4(A), the scooping surface 31a may protrude from the lower end of the lens contact area 31. By having the protrusion at the distal end of the scooping surface 31a, the end of the scooping surface 31a can be pushed in between the lens 2 and the lens setting section 8. Consequently, air can move to around the center of the lens 2, enabling the lens 2 to be easily released from the lens setting section 8.

Figure 4B:
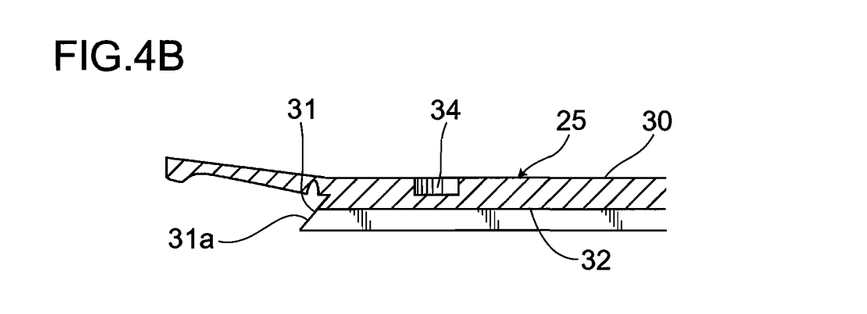

Alternatively, the scooping surface 31a may be formed to have a wedge-like shape, as shown in FIG. 4(B). By pushing in the wedge-shaped scooping surface 31a between the lens 2 and the lens setting section 8, the rear end of the lens 2 can be lifted upward. Consequently, the lens 2 can be easily released from the lens setting section 8.

The guide groove 32 is formed so as to allow the plunger 26 to slide thereon, and to allow the distal end of the plunger 26 to protrude from the lens contact area 31. The guide groove 32 is formed substantially in the center of one surface of the slider 25 over the entire length thereof, and comprises a groove that is parallel to the axial line A of lens movement. A cross section of the guide groove 32 is formed substantially in the same shape as the contour of the plunger 26. A fan-shaped leading passage 21a is formed at the proximal end of the guide groove 32. Thus, the push rod 27 is inserted through the guide groove 32 formed in the slider 25, and slides within the guide groove 32 in a longitudinal direction of the slider 25. Alternatively, the guide groove 32 may be a hole that pierces parallel to the axial line A of lens movement.

The slider body 30 enables the slider 25 to be held substantially in the center of the main body 3 while enabling the slider 25 to move along the axial line A of lens movement, by engaging with the slit 9. Therefore, the plunger 26 is held in the center of the main body 3, and movable along the axial line A of lens movement due to the presence of the guide groove 32. The handling element 33 enables easy movement of the slider 25.

The looped-member guide 34 is formed on another surface of the slider 25 on which the guide groove 32 is not formed. The looped-element guide 34 fixes the lens 2 by catching one of the looped haptic elements 2b. The looped-member guide 34 is formed by a groove similar to the curvature of the looped haptic elements 2b. The looped-member guide 34 is formed in the curvature on the side of the distal end of the slider 25 so as not to physically stress the looped haptic elements 2b.

Figure 5:
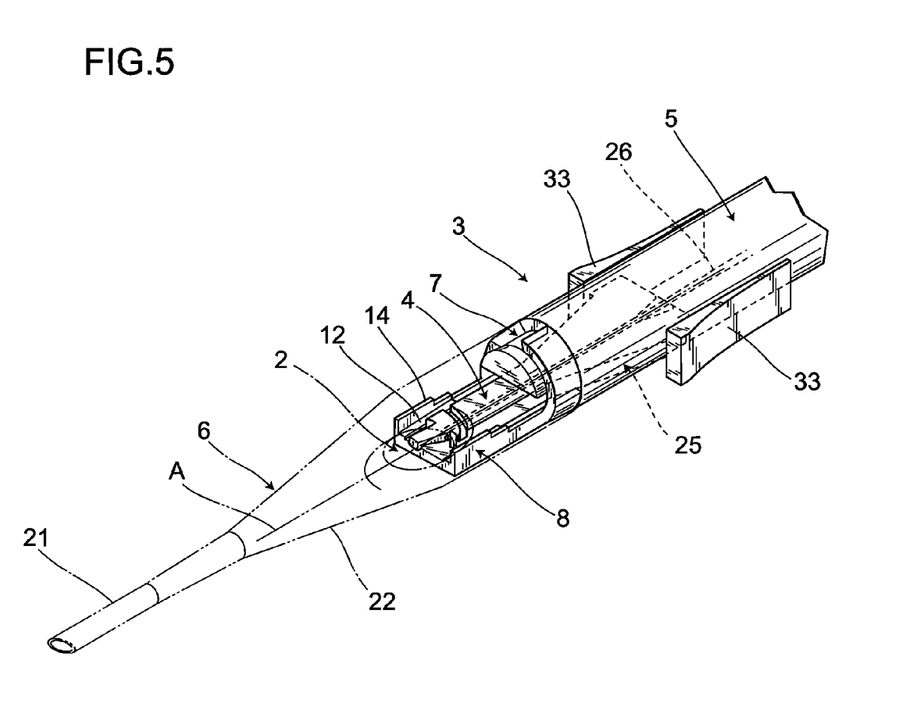
FIG. 5 is a perspective view showing a state in which a lens has been set on the lens setting section.

As shown in FIG. 5, the slider 25 has the handling element 33 for pushing the slider 25 in and out. The handling element 33 is a pair located on right and left sides of the axial line A of lens movement, and connected to an end of the slider body 30 while protruding from the proximal member 5. The handling element 33 is formed so as to bulge more when viewed toward the distal end of the main body 3. Although not shown in the drawings, the handling element 33 may have a corrugated surface formed by a plurality of grooves that are substantially perpendicular to the axial line A of lens movement. Alternatively, an arrow indicating a direction of movement may be shown on the surface.

Procedures of assembling the intraocular lens insertion instrument 1 of the above configuration will be described next. The slider 25 is firstly attached to the proximal member 5. In order to join the slider 25 and the proximal member 5, the slider body 30 is engaged with the slit 9 from the one end of the proximal member 5, and the slider 25 is pushed in to the proximal end of the slit 9. The plunger 26 is then inserted from the other end of the proximal member 5. At this time, the distal end of the plunger 26 is aligned with a position where the distal end does not project beyond the distal end of the slider 25 having been set in the proximal member 5. Thereafter, as shown in FIG. 3, one of the looped haptic elements 2b of the lens 2 is caught by the looped-element guide 34 of the slider 25, and the lens 2 is set on the lens setting section 8. At this time, as shown in FIG. 3(A), the lens 2 is held with the forward tilt by being set on the posture holding mount 12. By keeping the forward tilt of the lens 2, the looped haptic element 2b at the rear is set above the lens push-out mechanism 4. Furthermore, since the lens setting section 8 has the sidewalls 14, the center of the lens 2 can be easily aligned with the axial line A of lens movement. Thereafter, as shown in FIG. 5, the distal member 6 is united with the proximal member S in the engagement section 7. In this manner, the intraocular lens insertion instrument 1 can be securely assembled without stress on the lens 2.

Operation of the above configuration will be described next. The lens 2 has been set on the lens setting section 8 for some time, and in close contact with the lens setting section 8. Firstly, an operator holds the handling element 33 and pushes the slider 25 forward. When the slider 25 is pushed forward, the lens contact area 31 touches the lens 2. When the operator pushes the slider 25 forward in a state where the lens 2 is in contact with the lens contact area 31, the rear of the lens 2 is lifted since the lens 2 is held with the forward tilt. When the rear of the lens 2 is lifted, air comes in between the lens 2 and the lens setting section 8, releasing the lens 2 having been in close contact with the lens setting section 8 from the lens setting section 8. By pushing the slider 25 until the slider 25 hits the stopper that is not shown in FIG. 5, the lens 2 can be pushed out to the transition section 22.

When the slider 25 hits the stopper 23 and stops, the operator pushes the plunger 26. In order to push the plunger 26, the operator pushes the grip unit 28 to cause the female screw 29a to engage with the engagement projections 10 by screwing. Thereafter, the operator turns the grip unit 28. While being turned, the grip unit 28 moves from the proximal end of the proximal member 5 in a direction of the axial line A of lens movement. When the grip unit 28 is moved from the proximal end in the direction of the axial line A, the push rod 27 moves in the direction of the axial line A by being pushed by the grip unit 28, while pushing the plunger 26. In this manner, the lens 2 is folded while passing through the narrow nozzle piece 21 by being pushed by the plunger 26. By pushing the plunger 26 further in a state where the lens 2 is folded in such a manner, the lens 2 is inserted into an eye.

As has been described above, according to this embodiment, the intraocular lens insertion instrument 1 has the releasing means 11 for releasing the lens 2 pushed by the lens push-out mechanism 4 from the lens setting section 8. Therefore, the lens 2 in close contact with the lens setting section 8 can be released from the lens setting section 8 when the lens push-out mechanism 4 pushes the lens 2. Consequently, the lens 2 can be pushed out smoothly, which prevents damage to the lens 2 as well as unstable behavior of the lens 2.

Moreover, the releasing means 11 has the posture holding mount 12 for holding the lens 2 with the forward tilt along the direction of the axial line A of lens movement. Therefore, when the lens push-out mechanism 4 pushes the lens 2, the rear end of the lens 2 is lifted, allowing air to come in between the lens 2 and the lens setting section 8. In this manner, the lens 2 can be released from the lens setting section 8 and pushed out smoothly.

Since the posture holding mount 12 has the passage 15 through which the lens push-out mechanism 4 passes, the posture holding mount 12 does not hinder the movement of the lens push-out mechanism 4 when the lens push-out mechanism 4 pushes out the lens 2. Therefore, the lens 2 can be pushed out more smoothly.

Furthermore, the lens push-out mechanism 4 has the scooping surface 31a for scooping the lens 2. Therefore, when the lens 2 is pushed out, the scooping surface 31a scoops the rear end of the lens 2, allowing air to come in between the lens 2 and the lens setting section 8. Consequently, the lens 2 can be released from the lens setting section 8 and pushed out smoothly.

In addition, the posture holding mount 12 is configured to support the both sides of the lens 2. Therefore, even in the case where the lens 2 has been stored for a long time, deformation of the optic 2a can be prevented.

Since the posture holding mount 12 holds the lens 2 with the forward tilt, the looped haptic element 2b at the rear of the lens 2 can be placed above the lens push-out mechanism 4. Therefore, damage to the looped haptic elements 2b associated with the movement of the lens push-out mechanism 4 can be prevented.

Moreover, the lens setting section 8 has the sidewalls 14. Therefore, the lens 2 can be set easily at the center of the lens setting section 8. Consequently, the center of the lens 2 agrees with the axial line A of lens movement, which enables smoother push-out of the lens 2.

In a state of non-use, the lens 2 is in close contact with the lens setting section 8. Therefore, the lens 2 can be held safely and securely even in the case where the looped haptic element 2b is not caught by the looped-element guide 34 of the slider 25.

The present invention is not limited to the embodiment described above, and various modifications can be made thereto within the scope of the present invention.

The invention claimed is:

1. An intraocular lens insertion instrument comprising:
a main body including a lens setting section that is configured to store an unstressed intraocular lens thereon, a transition section for deforming the intraocular lens, and a nozzle piece for discharging the intraocular lens;
a slider that moves distally toward the transition section and pushes the unstressed intraocular lens distally from the lens setting section to the transition section, thereby folding the intraocular lens;
a releasing device releasing the intraocular lens pushed by the slider from the lens setting section, wherein the releasing device includes
a posture holding mount holding the lens such that an edge of the lens closest to the nozzle piece is lower in elevation relative to an opposite edge of the lens farthest from the nozzle piece, resulting in the lens having a forward tilt relative to an axial line of lens movement,
wherein the posture holding mount includes
a slope inclined downwards toward the nozzle piece; and
a groove through which the slider passes; and
a plunger that pushes the folded intraocular lens distally from the transition section and through the nozzle piece;
wherein the slider and the plunger are associated with one another such that the slider is distally movable relative to the plunger, and the plunger is distally movable relative to and distal of the slider.

2. The intraocular lens insertion instrument according to claim 1, wherein the posture holding mount has a passage through which the slider passes.

3. The intraocular lens insertion instrument according to claim 2, wherein the slider has a scooping surface for scooping the lens.

4. The intraocular lens insertion instrument according to claim 1, wherein the slider has a scooping surface for scooping the lens.

5. The intraocular lens insertion instrument according to claim 1, wherein the lens is disposed at the lens setting section beforehand when the intraocular lens insertion device is shipped.

6. The intraocular lens insertion instrument according to claim 1, wherein the groove is parallel to the axial line of lens movement.

7. An apparatus as claimed in claim 1, wherein
the slider includes a guide groove in which a portion of the plunger is located.

8. An apparatus, comprising:
a main body defining a lens movement direction and including a lens setting section, a nozzle, and a tapered transition section between the lens setting section and the nozzle, the lens setting section having a first and second longitudinally extending members, separated by a groove, that slope downward toward the nozzle;
an intraocular lens stored on the first and second longitudinally extending members in a substantially unstressed state with an edge closest to the nozzle lower in elevation than an opposite edge farthest from the nozzle;
a slider carried within the main body and movable in the lens movement direction to drive the intraocular lens from the lens setting section to the tapered transition section; and
a plunger carried within the main body and movable in the lens movement direction to drive the intraocular lens from the tapered transition section and through the nozzle;
wherein the slider and the plunger are associated with one another such that the slider is distally movable relative to the plunger, and the plunger is distally movable relative to and distal of the slider.

9. An apparatus as claimed in claim 8, wherein the slider is carried within the main body such that a portion of the slider will be located within the groove in the lens setting section as the slider drives the intraocular lens from the lens setting section to the tapered transition section.

10. An apparatus as claimed in claim 8, wherein
the slider includes a lens contact area; and
the plunger is narrower than the lens contact area.

11. An apparatus as claimed in claim 8, wherein
the slider includes a guide groove in which a portion of the plunger is located.

12. An apparatus as claimed in claim 8, wherein
the slider includes a scooping surface.

13. An apparatus as claimed in claim 12, wherein
the intraocular lens includes an outer surface with a radius of curvature; and
the slider scooping surface comprises an arcuate surface with a radius of curvature that is substantially the same as the intraocular lens outer surface radius of curvature.

14. An apparatus as claimed in claim 8, further comprising:
a slider handle located adjacent to the main body and connected to the slider; and
a plunger grip located proximal of the main body and connected to the plunger.

15. An apparatus as claimed in claim 14, wherein
the slider handle includes first and second handle members located on opposite sides of the main body.

16. An apparatus as claimed in claim 14, wherein
the plunger grip is rotatable.

17. An apparatus as claimed in claim 8, wherein
the first and second longitudinally extending members support diametrically opposed edges of the intraocular lens.

\* \* \* \* \*